United States Patent
Johnson et al.

(10) Patent No.: US 8,753,333 B2
(45) Date of Patent: *Jun. 17, 2014

(54) SYSTEM FOR DETERMINING PROXIMITY RELATIVE TO A NERVE

(75) Inventors: Kristin D. Johnson, Louisville, CO (US); Scott F. Alexander, Westminster, CO (US); Jeffrey M. Roy, Boulder, CO (US); Rebecca J. Coulson, Lyons, CO (US)

(73) Assignee: Covidien LP, Mansfield, MA (US)

( * ) Notice: Subject to any disclaimer, the term of this patent is extended or adjusted under 35 U.S.C. 154(b) by 163 days.

This patent is subject to a terminal disclaimer.

(21) Appl. No.: 13/179,728

(22) Filed: Jul. 11, 2011

(65) Prior Publication Data

US 2011/0270121 A1 Nov. 3, 2011

Related U.S. Application Data

(63) Continuation-in-part of application No. 12/720,881, filed on Mar. 10, 2010, now Pat. No. 8,623,004.

(51) Int. Cl.
*A61B 18/18* (2006.01)

(52) U.S. Cl.
USPC ............................. 606/32; 606/34

(58) Field of Classification Search
USPC ............................. 606/32, 34, 42
See application file for complete search history.

(56) References Cited

U.S. PATENT DOCUMENTS

| | | | |
|---|---|---|---|
| 4,543,959 A | 10/1985 | Sepponen | |
| 4,962,766 A * | 10/1990 | Herzon | 600/554 |
| 5,080,104 A * | 1/1992 | Marks et al. | 600/461 |
| 5,284,154 A * | 2/1994 | Raymond et al. | 600/554 |
| 5,762,609 A | 6/1998 | Benaron | |
| 5,800,350 A | 9/1998 | Coppleson et al. | |
| 5,928,158 A * | 7/1999 | Aristides | 600/547 |
| 6,109,268 A | 8/2000 | Thapliyal | |
| 6,241,725 B1 | 6/2001 | Cosman | |
| 6,264,653 B1 * | 7/2001 | Falwell | 606/41 |
| 6,355,032 B1 * | 3/2002 | Hovda et al. | 606/32 |
| 6,428,537 B1 | 8/2002 | Swanson et al. | |
| 6,466,817 B1 * | 10/2002 | Kaula et al. | 600/546 |

(Continued)

FOREIGN PATENT DOCUMENTS

| | | |
|---|---|---|
| EP | 1181895 | 2/2002 |
| EP | 1946713 | 7/2008 |
| WO | WO 2006/042117 | 4/2006 |

OTHER PUBLICATIONS

Copy of International Search Report from European Application No. 11157635 date of completion Jul. 25, 2011.

(Continued)

*Primary Examiner* — Linda Dvorak
*Assistant Examiner* — Jocelyn D Ram (57) ABSTRACT

A system for determining proximity of a surgical device relative to nerve structure includes at least one surgical device having a sensor assembly operably coupled to a processing unit and configured to transmit at least one electrical signal generated by the processing unit through nerve structure to elicit a measurable response there from. The processing unit is configured to calculate a signature property value of nerve structure based on the measurable response and to determine proximity of the nerve structure to the surgical device based on the measurable response. The processing unit is further configured to test the nerve function after completing the surgical procedure.

8 Claims, 7 Drawing Sheets

(56) References Cited

U.S. PATENT DOCUMENTS

| | | | |
|---|---|---|---|
| 6,546,270 | B1 | 4/2003 | Goldin et al. |
| 6,569,160 | B1 | 5/2003 | Goldin et al. |
| 6,760,616 | B2 * | 7/2004 | Hoey et al. .................. 600/547 |
| 7,089,045 | B2 | 8/2006 | Fuimaono et al. |
| 7,099,712 | B2 | 8/2006 | Fuimaono et al. |
| 7,155,270 | B2 | 12/2006 | Solis et al. |
| 7,207,989 | B2 | 4/2007 | Pike, Jr. et al. |
| 7,228,164 | B2 | 6/2007 | Fuimaono et al. |
| 7,257,434 | B2 | 8/2007 | Fuimaono et al. |
| 7,257,435 | B2 | 8/2007 | Plaza |
| 7,302,285 | B2 | 11/2007 | Fuimaono et al. |
| 7,522,953 | B2 | 4/2009 | Kaula et al. |
| 7,819,860 | B2 * | 10/2010 | Wittenberger et al. ......... 606/23 |
| 8,050,769 | B2 * | 11/2011 | Gharib et al. .................. 607/48 |
| 8,068,912 | B2 * | 11/2011 | Kaula et al. .................. 607/48 |
| 2003/0045798 | A1 | 3/2003 | Hular et al. |
| 2003/0045808 | A1 * | 3/2003 | Kaula et al. .................. 600/546 |
| 2005/0027199 | A1 | 2/2005 | Clarke |
| 2006/0106375 | A1 | 5/2006 | Werneth et al. |
| 2006/0241577 | A1 * | 10/2006 | Balbierz et al. ................. 606/32 |
| 2007/0016097 | A1 * | 1/2007 | Farquhar et al. .............. 600/546 |
| 2007/0066971 | A1 | 3/2007 | Podhajsky |
| 2007/0106289 | A1 * | 5/2007 | O'Sullivan ..................... 606/41 |
| 2007/0156128 | A1 | 7/2007 | Jimenez |
| 2007/0248254 | A1 | 10/2007 | Mysore Siddu et al. |
| 2008/0281313 | A1 * | 11/2008 | Fagin et al. .................... 606/34 |
| 2009/0163904 | A1 * | 6/2009 | Miller et al. ................... 606/33 |
| 2009/0204016 | A1 | 8/2009 | Gharib et al. |
| 2009/0267773 | A1 | 10/2009 | Markowitz et al. |
| 2009/0275827 | A1 | 11/2009 | Aiken |
| 2011/0224543 | A1 * | 9/2011 | Johnson et al. ............... 600/426 |
| 2011/0224668 | A1 * | 9/2011 | Johnson et al. ................ 606/42 |
| 2011/0270121 | A1 * | 11/2011 | Johnson et al. ............... 600/554 |
| 2011/0275952 | A1 * | 11/2011 | Johnson et al. ............... 600/547 |

OTHER PUBLICATIONS

European Search Report No. 11157632.8 dated Aug. 8, 2011.

* cited by examiner

SYSTEM FOR DETERMINING PROXIMITY RELATIVE TO A NERVE

CROSS-REFERENCE TO RELATED APPLICATION

The present application is a continuation-in-part of a U.S. application Ser. No. 12/720,881 entitled "System and Method for Determining Proximity Relative to a Critical Structure" filed on Mar. 10, 2010, which is hereby incorporated by reference in its entirety.

BACKGROUND

1. Technical Field

The present disclosure relates to open or endoscopic surgical instruments and methods for treating tissue. More particularly, the present disclosure relates to a system and method for determining proximity of a surgical device relative to nerve tissue by monitoring nerve responses.

2. Background of Related Art

A hemostat or forceps is a simple plier-like tool that uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Over the last several decades, more and more surgeons are complementing traditional open methods of gaining access to vital organs and body cavities with endoscopes and endoscopic instruments that access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the cannulas.

As mentioned above, by utilizing an electrosurgical instrument, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

Bipolar electrosurgical instruments are known in the art, as are other electrosurgical instruments. Commonly-owned U.S. Patent Application Publication No. 2007-0062017, discloses a bipolar electrosurgical instrument. Conventional bipolar electrosurgical instruments may include a cutting blade, fluid applicator, stapling mechanism or other like feature, in various combinations.

Different types of anatomical structures, i.e. vessels, ducts, organs, may require different energy delivery configurations to effect proper treatment. While a specific energy delivery configuration may be adequate for treating an artery or vein, the same energy delivery configuration may not be suitable for treating a duct. Also, if a surgical device is too close to a non-target nerve structure when energy is supplied to the surgical device, then the nerve structure may be damaged.

During certain procedures, surgeons must identify critical anatomical structures such as large vasculature or urinary or bile ducts. These structures typically need to be avoided or ligated during a procedure, thus requiring a high degree of confidence when identifying such structures.

One complication during laparoscopic procedures in particular, is inadvertently engaging nearby critical anatomical structures due to quick or abrupt movement of instruments within the surgical site, poor visibility, lack of tactile response, confusion of the anatomy from patient to patient, or inadequate control of the instrumentation being utilized to perform the procedure. For example, when performing a thyroidectomy to remove a thyroid gland, the recurrent laryngeal nerve (RLN) needs to be located and preserved. The RLN controls motor function and sensation of larynx (voice box). Identifying and avoiding this structure is important for a successful surgical outcome.

Traditional methods for identifying anatomical structures within the body are based on sensing physical characteristics or physiological attributes of body tissue, and then distinguishing normal from abnormal states from changes in the characteristic or attribute. For example X-ray techniques measure tissue physical density, ultrasound measures acoustic density, and thermal sensing techniques measures differences in tissue heat.

Signature properties of nerve structures such as electrical conductivity, impedance, thermal conductivity, permittivity, and capacitance may be measured and compared to known data to determine proximity of the non-target nerve structure to the surgical device and to distinguish anatomical structures from other anatomical structures and/or known data. If these signature properties can be properly elicited from a nerve structure, measureable values that correspond to these elicited properties may be calculated and compared to known values for purposes of identifying and detecting proximity to the nerve structure.

SUMMARY

According to an embodiment of the present disclosure, a system for determining proximity of a surgical device relative to nerve structure includes at least one surgical device having a sensor assembly operably coupled to a processing unit. The sensor assembly is configured to transmit at least one electrical signal generated by the processing unit through nerve structure to elicit a measurable response there from. The processing unit is configured to calculate a signature property value of nerve structure based on the measurable response and to determine proximity of the at least one surgical device relative to the target anatomical structure based on a comparison between the signature property value and at least one other signature property.

According to another embodiment of the present disclosure, a method for determining proximity of a surgical device relative to nerve structure includes the steps of placing at least one surgical device having a sensor assembly disposed thereon relative to a target anatomical structure and transmitting at least one electrical signal from the sensor assembly to elicit a measurable response from nerve structure. The method also includes the steps of calculating one or more signature properties of nerve structure based on the measureable response and comparing values of the one or more measured signature properties to at least one other measured signature property. The method also includes the step of determining proximity of the at least one surgical device relative to nerve structure based on the comparison between the one or more measured signature properties and at least one other measured signature property.

According to another embodiment of the present disclosure, a method for determining proximity of nerve structure during an electrosurgical procedure includes the steps of placing at least one surgical device having a sensor assembly disposed thereon relative to a target anatomical structure and transmitting at least one electrical signal from the sensor assembly to elicit a measurable response from nerve structure. The method also includes the steps of calculating a signature property of nerve structure based on the measureable response and determining proximity of the surgical device to nerve structure based on the measurable response. The method also includes the step of selectively applying energy to the target anatomical structure to perform electrosurgical procedure in response to determining proximity of the surgical device is not too close to the nerve structure.

BRIEF DESCRIPTION OF THE DRAWINGS

Various embodiments of the subject instrument are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

An electrosurgical generator according to the present disclosure can perform monopolar and bipolar electrosurgical procedures, including anatomical tissue ligation procedures. The generator may include a plurality of outputs for interfacing with various bipolar and monopolar electrosurgical instruments (e.g., laparoscopic electrodes, return electrodes, electrosurgical forceps, footswitches, etc.). Further, the generator includes electronic circuitry configured to generate electrosurgical energy (e.g., RF, microwave, ultrasonic, etc.) specifically suited for various electrosurgical modes (e.g., cut, coagulate (fulgurate), desiccate, etc.) and procedures (e.g., ablation, vessel sealing, etc.).

The present disclosure generally relates to a system for identifying a nerve structure, which may be included in an existing surgical device, e.g. forceps, a monpolar electrode, or articulating robotic (automatic) instruments or systems, or a stand alone device. The system transmits one or more electrical signals from a sensor assembly disposed on one or more surgical instruments through the nerve structure to elicit a measureable response therefrom. The one or more electrical signals may be sent periodically, continuously, and/or selected by a user. Based on the response, the system calculates one or more signature property values of the nerve structure and compares these values to known signature property values of various structures from which a measurable response has been elicited. Based on the comparison, the system identifies and determines proximity of the surgical device to the nerve structure and alerts a user of the system as to the distance of the nerve structure relative to the sensor assembly of the surgical device. Additionally, after a surgical procedure is performed, the nerve structure may be tested to ensure the nerve was not damaged by the surgical procedure. The nerve may be tested by sending a small electrical pulse from the surgical device and measuring the response received from the nerve structure.

Figure 1A:
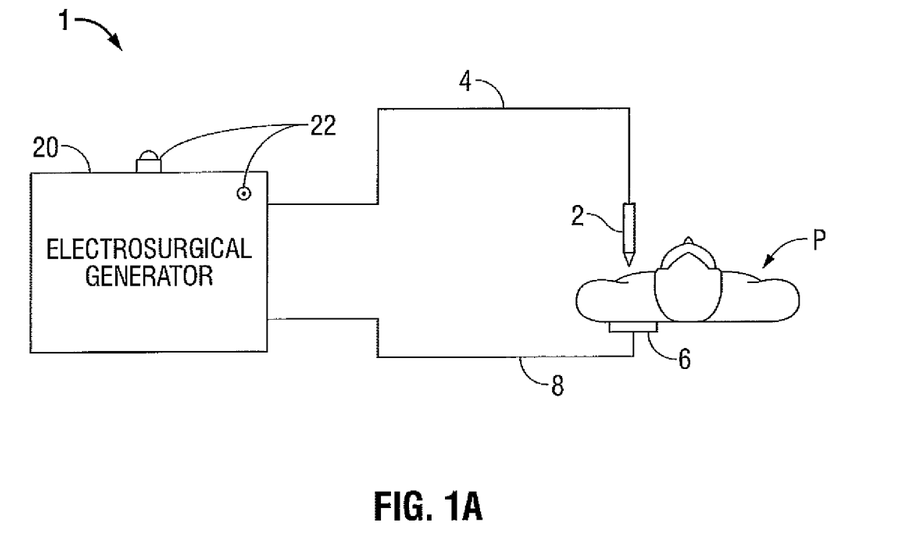
FIG. 1A is a schematic block diagram of a monopolar electrosurgical system in accordance with an embodiment of the present disclosure.

FIG. 1A is a schematic illustration of a monopolar electrosurgical system 1 according to one embodiment of the present disclosure. The system 1 includes an electrosurgical instrument 2 having one or more electrodes for treating tissue of a patient P. The instrument 2 is a monopolar type instrument (e.g., electrosurgical cutting probe, ablation electrode(s), etc.) including one or more active electrodes. Electrosurgical energy is supplied to the instrument 2 by a generator 20 via a supply line 4 that is connected to an active terminal 30 (FIG. 2) of the generator 20, allowing the instrument 2 to coagulate, cut, ablate, and/or otherwise treat tissue. The electrosurgical energy is returned to the generator 20 through a return electrode 6 via a return line 8 at a return terminal 32 (FIG. 2) of the generator 20.

Figure 1B:
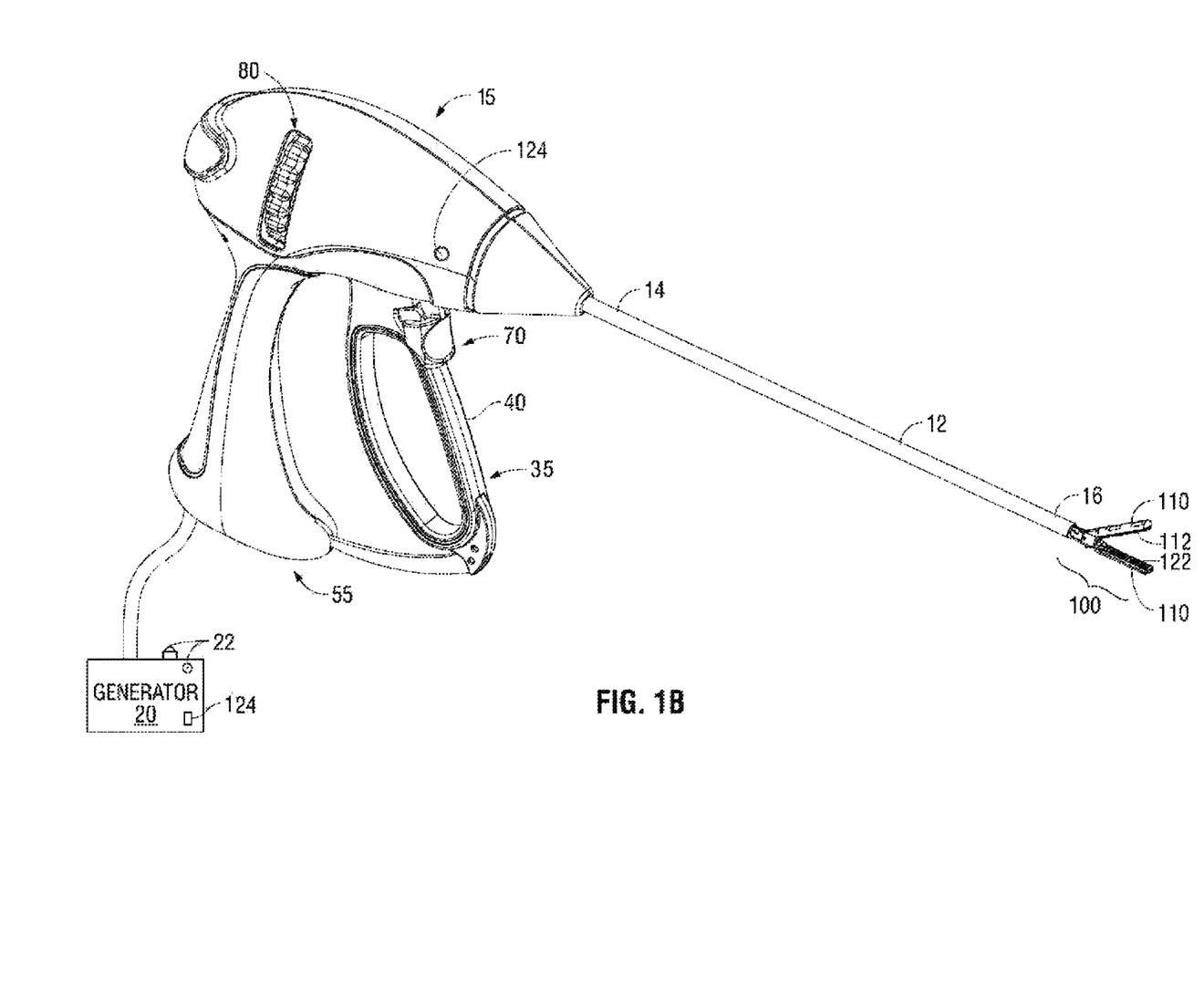
FIG. 1B is a schematic block diagram of a bipolar electrosurgical system in accordance with an embodiment of the present disclosure.

Turning now to FIG. 1B, an instrument generally identified as bipolar forceps 10 is for use with various surgical procedures and includes a housing 15, a handle assembly 35 including a moveable handle 40 relative to a fixed handle 55, a rotating assembly 80, a trigger assembly 70, and an end effector assembly 100 that mutually cooperate to grasp, seal, and divide tubular vessels and vascular tissues. Forceps 10 includes a shaft 12 that has a distal end 16 dimensioned to mechanically engage the end effector assembly 100 and a proximal end 14 that mechanically engages the housing 15. The end effector assembly 100 includes opposing jaw members 110 and 120 that cooperate to effectively grasp tissue for treatment purposes. With this purpose in mind, jaw members 110 and 120 include active electrodes 112 and 122 disposed thereon in a bipolar configuration. Active electrodes 112, 122 are operably coupled to generator 20 and are configured to selectively apply electrosurgical energy supplied from the generator 20 to tissue grasped between the jaw members 110, 120. The end effector assembly 100 may be designed as a unilateral assembly, e.g., jaw member 120 is fixed relative to the shaft 12 and jaw member 110 pivots relative to jaw member 120 to grasp tissue, or as a bilateral assembly, e.g., jaw members 110 and 120 pivot relative to each other to grasp tissue.

Examples of forceps are shown and described in commonly-owned U.S. application Ser. No. 10/369,894 entitled "VESSEL SEALER AND DIVIDER AND METHOD MANUFACTURING SAME" and commonly-owned U.S. application Ser. No. 10/460,926 (now U.S. Pat. No. 7,156, 846) entitled "VESSEL SEALER AND DIVIDER FOR USE WITH SMALL TROCARS AND CANNULAS".

Although the following disclosure focuses predominately on discussion of electrosurgical instruments for use in connection with endoscopic surgical procedures, open type instruments are also contemplated for use in connection with traditional open surgical procedures. Additionally and as discussed in greater detail below, the aspects of the present disclosure may be incorporated into any suitable electrosurgical instrument (e.g., instrument 2, forceps 10) or any suitable non-electrosurgical instrument (e.g., probes, graspers, prods, clamps, grips, forceps, pliers, cutters, electrocautery devices, etc.).

Figure 2:
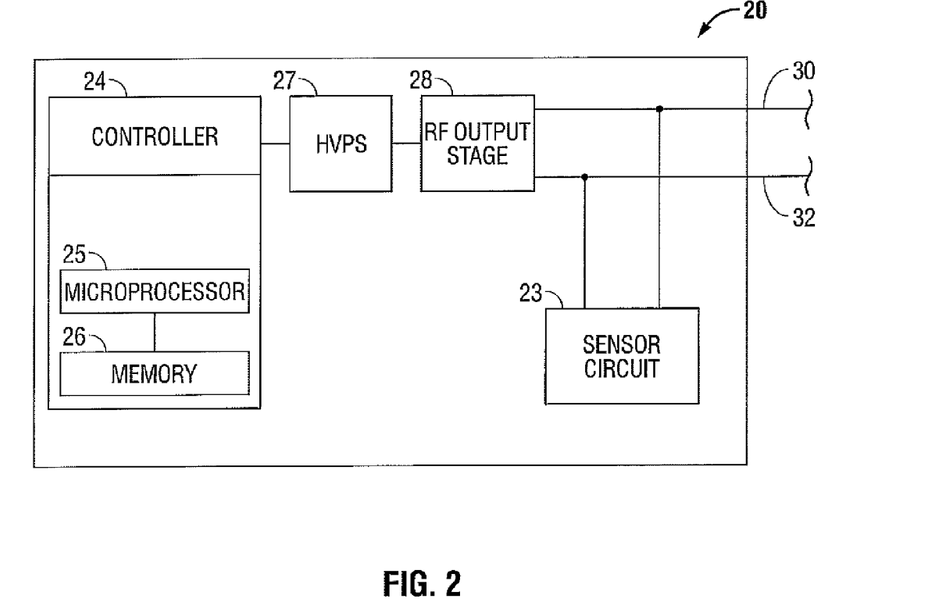
FIG. 2 is a schematic block diagram of a generator in accordance with an embodiment of the present disclosure.

FIG. 2 shows a schematic block diagram of the generator 20 having a controller 24, a high voltage DC power supply 27 ("HVPS"), a sensor module 23, and an energy output stage 28 configured to output electrosurgical energy (e.g., microwave, RF, etc.) from generator 20. The HVPS 27 is connected to a conventional AC source (e.g., electrical wall outlet) and provides high voltage DC power to the energy output stage 28, which then converts high voltage DC power into electrosurgical energy for delivery to the active electrode(s) of an electrosurgical instrument (e.g., instrument 2, forceps 10, etc.) via the active terminal 30. In certain embodiments (FIGS. 1A and 1B), the electrosurgical energy is returned to the generator 20 via the return terminal 32.

The generator 20 may include a plurality of connectors to accommodate various types of electrosurgical instruments (e.g., instrument 2, electrosurgical forceps 10, etc.). Further, the generator 20 may operate in monopolar or bipolar modes by including a switching mechanism (e.g., relays) to switch the supply of electrosurgical energy between the connectors, such that, for instance, when the monopolar type instrument 2 is connected to the generator 20, only the monopolar plug receives electrosurgical energy.

The controller 24 includes a processing unit 25 operably connected to a memory 26, which may be a volatile type memory (e.g., RAM) and/or a non-volatile type memory (e.g., flash media, disk media, etc.). The processing unit 25 may be any logic processor or analog circuitry (e.g., microprocessor, control circuit, etc.) adapted to perform the calculations discussed in the present disclosure. The processing unit 25 includes an output port that is operably connected to the HVPS 27 and/or the energy output stage 28 allowing the processing unit 25 to control the output of the generator 20 according to either open and/or closed control loop schemes.

A closed loop control scheme generally includes a feedback control loop wherein the sensor module 23 provides feedback to the controller 24 (e.g., information obtained from one or more sensing mechanisms that sense various parameters such as impedance, temperature, tissue conductivity, permittivity, output current, and/or voltage, etc.). The controller 24 then signals the power supply 27, which then adjusts the DC power supplied to the RF output stage 28, accordingly. The controller 24 also receives input signals from the input controls of the generator 20 and/or instrument 2 or forceps 10. The controller 24 utilizes the input signals to adjust the power output of the generator 20 and/or instructs the generator 20 to perform other control functions. In some embodiments, the generator 20 may utilize audio-based and/or a video-based display to inform the user of the sensed tissue parameters in the field of view of the one or more sensing mechanisms.

The processing unit 25 is capable of executing software instructions for processing data received by the sensor module 23, and for outputting control signals to the generator 20 or other suitable operating room devices (e.g., camera monitor, video display, audio output, etc.), accordingly. The software instructions, which are executable by the controller 24, are stored in the memory 26 of the controller 24. The controller 24 may include analog and/or logic circuitry for processing the sensed values and determining the control signals that are sent to the generator 20, rather than, or in combination with, the processing unit 25.

In some embodiments, generator 20 and processing unit 25 may be separate stand-alone units operably connected to each other (not shown) or processing unit 25 may be incorporated within generator 20, as shown in FIG. 2. In some embodiments, processing unit 25 may be incorporated within the surgical device being used during a procedure (e.g., instrument 2, forceps 10). In this scenario, the signal-to-noise ratio of signals transmitted to and from processing unit 25 may be improved since the signals may experience a decrease in losses caused by travel through relatively long lengths of cable. For ease of disclosure, generator 20 is described as incorporating processing unit 25 and processing unit 25 is, in turn, described as being incorporated within generator 20.

Processing unit 25 is operably connected to an electrode or sensor assembly that includes one or more transmitting electrodes 50a and one or more receiving electrodes 50b. The sensor assembly (hereinafter referred to as "sensor assembly 50a, 50b") may be mounted on one or more suitable electrosurgical instruments such as, for example, monopolar instrument 2 or forceps 10, or on one or more suitable non-electrosurgical instruments such as, for example, a grasper, a dissector, a probe, or a catheter (not shown). In this scenario, the generator 20 may include a plurality of connectors to accommodate non-electrosurgical instruments such that a sensor assembly 50a, 50b mounted to such an instrument may communicate with the generator 20 and/or the processing unit 25 for purposes of identifying target anatomical structures.

Sensor assembly 50a, 50b is configured to sense and/or measure various properties of nerve structures such as, without limitation, electrical conductivity, thermal conductivity, fluid flow, temperature, capacitance, permittivity, voltage, current, optical-based information, etc. With these purposes in mind, sensor assembly 50a, 50b may be embodied as an impedance sensor, a temperature sensor, an optical sensor, a capacitance sensor, a permittivity sensor, a voltage sensor, a current sensor, a pressure sensor, or a combination of any two or more thereof.

In some embodiments, sensor assembly 50a, 50b may be mounted on a distal end of one or more electrosurgical and/or non-electrosurgical instruments such that the sensor assembly 50a, 50b may be used to sense ahead to the area that the user is moving the treatment device (e.g., instrument 2, forceps 10) to prevent incidental contact between surgical instruments and critical nerve structures, as discussed hereinabove.

Figure 4:
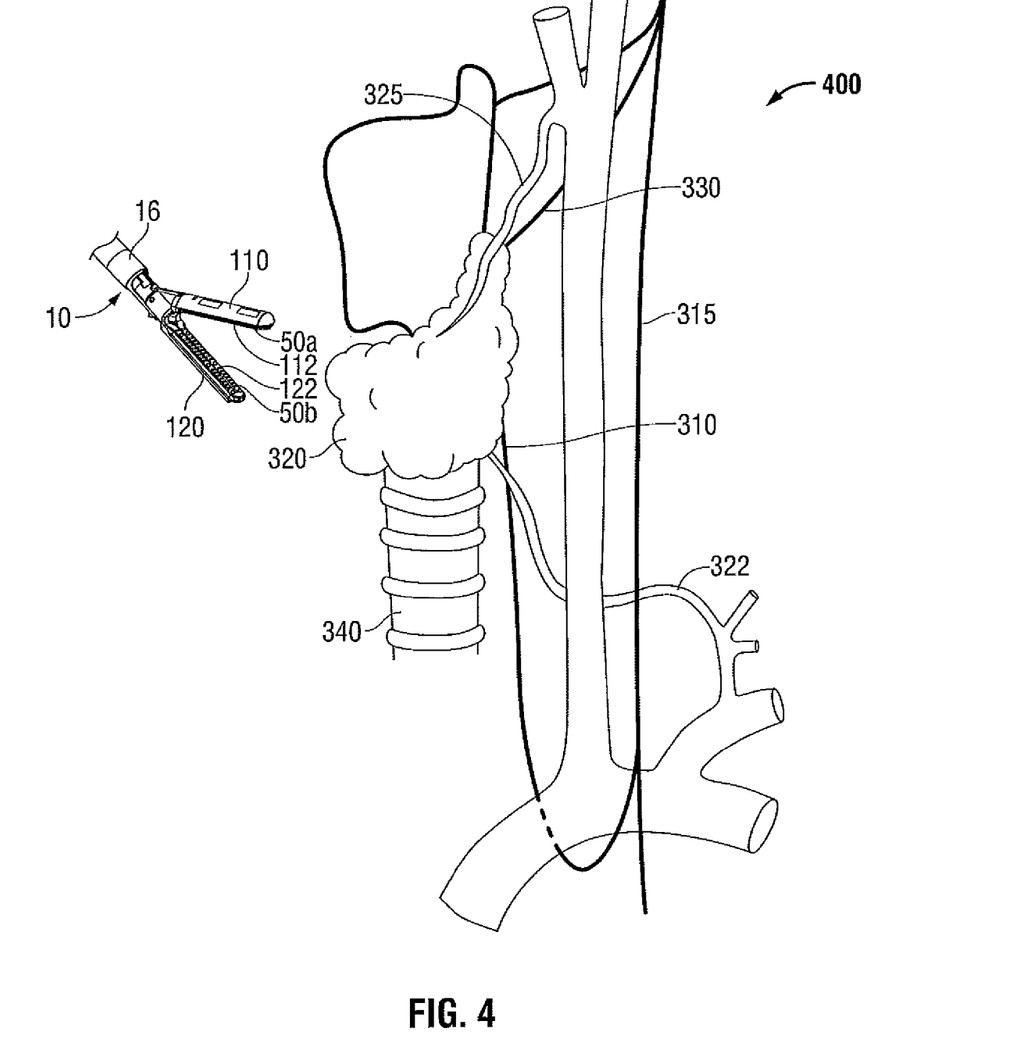
FIG. 4 is a perspective view of a bipolar forceps disposed relative to a thyroid region of a patient in accordance with another embodiment of the present disclosure.

In certain embodiments, the transmitting electrode 50a and the receiving electrode 50b may be substituted by the active electrodes (e.g., 112, 122) of an electrosurgical instrument utilized in the procedure such as forceps 10, shown by way of example in FIG. 4. Either of electrodes 112, 122 may be the transmitting electrode 50a and the other electrode 112, 122 may be the receiving electrode 50b. In this manner, active electrodes 112, 122 may be utilized to sense nerve structure so that the user may identify the nerve structure prior to the application of treatment energy to a gland, tissue or other anatomical structure and avoid inadvertent treatment to surrounding nerve structures or other critical anatomical structures. In one embodiment, each of the active electrodes 112, 122 may be split into more than one active electrode. This configuration allows smaller predefined surface areas that are configured to source and/or receive the electrical signal through anatomical structures and, thus, may be more suitable in larger jaw instruments. Additionally or alternatively, an insulative material (not shown) may be disposed between the jaw members 110, 120 to limit the surface area of the active electrodes 112, 122. Embodiments of the present disclosure are not limited to the methods of determining the signature properties disclosed herein. Any suitable method for measuring signature properties of anatomical structures, whether electrical, thermal, optical, or the like, may be incorporated into the embodiments of the present disclosure.

In use, a predetermined energy signal is periodically produced by the processing unit 25 and applied to the patient P through the transmitting electrode 50a, 112 and received by the receiving electrode 50b, 122. The resultant response from a nerve structure or other anatomical structure is processed by the processing unit 25 and is then measured and converted into a value of to determine proximity and/or identity of the nerve structure or other anatomical structure. For example, and without limitation, electrical conductivity, thermal conductivity, hydraulic conductivity, impedance, capacitance, and permittivity are all signature properties by which a nerve structure may be used in determining proximity.

In operation of one embodiment of the present disclosure, sensor assembly 50a, 50b is placed in contact with or in proximity to where the surgical procedure is performed. Processing unit 25 produces an electric signal that is directed around the surgical device through transmitting electrode 50a. Processing unit 25 may be configured to continuously or periodically produce a signal, or instead the instrument being utilized (e.g., bipolar forceps 10) may include a button or lever 124 mounted on housing 15 and/or generator 20 (FIG. 1B) for activating processing unit 25. As discussed above, depending on the application, the electric signal may be of a specific frequency or range of frequencies and of any configuration. In this manner, conductive nerve structures 310, 315, 330 may be utilized to transmit the electric signal a longer distance between the transmitting and receiving electrodes 50a and 50b such that transmitting and receiving electrodes 50a and 50b need not be in close proximity to each other to complete a circuit therebetween. These portions of the nerve structure 310, 315, 330 produce characteristic responses based on the signals delivered to electrode 50a by processing unit 25. The resulting response is acquired by receiving electrode 50b. Based on the response, the processing unit 25 calculates signature property values of the responding structure. By comparing the signature property values of the responding structure with signature property values of other structures and/or with known values of various structures, the identity of the responding structure may be identified along with the proximity of electrode 50a to the responding structure, which may include determining proximity to a nerve structure.

Additionally, electrodes 50a and 50b may be used to identify a target anatomical structure, then a treatment device such as bipolar forceps 10 may operate as a conventional bipolar vessel sealer. The energy delivery configuration of generator 20 may be adjusted in accordance with the identified anatomical structure being treated. The closure pressure of the opposing jaw members 110, 120 may also be adjusted in view of the anatomical structure being sealed.

The electrical current produced by the processing unit 25 may vary depending on the type of tissue and/or the anatomical structure (e.g., duct, vasculature, vessel, organ, etc.) being identified. Processing unit 25 is configured to produce AC and/or DC current. Processing unit 25 may be configured to generate an electrical signal having a frequency ranging from RF (100 kHz) freq. upwards of microwaves (low MHz to GHz) freq. More specifically, the processing unit can generate an electrical signal from about 20 Hz to about 3.3 MHz. Depending on the application, processing unit 25 may produce a signal of constant frequency, a cascaded pulse interrogation signal (e.g., a cosign-shaped pulse), or may instead perform a frequency sweep or amplitude sweep.

More than one sensor assembly 50a, 50b may be connected to the processing unit 25. In this manner, the one or more sensor assemblies 50a, 50b of a particular instrument may include different electrode configurations depending on the anatomical structure being treated on and/or signal frequency being tested. Processing unit 25 may include any suitable methods of increasing the accuracy and consistency of the signature tissue property measurements, e.g., filters and multi-frequency readings.

Processing unit 25 may operate in a number of modes. For example, processing unit 25 may be configured to alert a user when sensor assembly 50a, 50b has contacted a specific nerve structure (e.g., vasculature, duct, vessel, tissue, organ, etc.). In this manner, a user would set processing unit 25 to scan for a particular signature property (e.g., electrical conductivity, thermal conductivity, capacitance, impedance, etc.). Processing unit 25 produces an electrical signal configured to best identify the signature tissue property and/or a known nerve structure inadvertently damaged during a surgical procedure. The electrical signal produced by processing unit 25 may be manually determined by the user or may instead be automatically determined by processing unit 25. The electrical signal produced may include a specific frequency or range of frequencies and/or may include a specific signal configuration. Sensor assembly 50a, 50b may be placed in contact over a portion of tissue or in close proximity thereto. As sensor assembly 50a, 50b contacts or approaches a nerve structure 310, 315, or 330, as determined by processing unit 25, processing unit 25 may alert the user. The alert may be audio and/or visual. With this purpose in mind, an audio and/or visual indicator 22 (FIGS. 1A and 1B) may be included in/on the generator 20 and/or the instrument utilized in the procedure (not explicitly shown).

Figure 3:
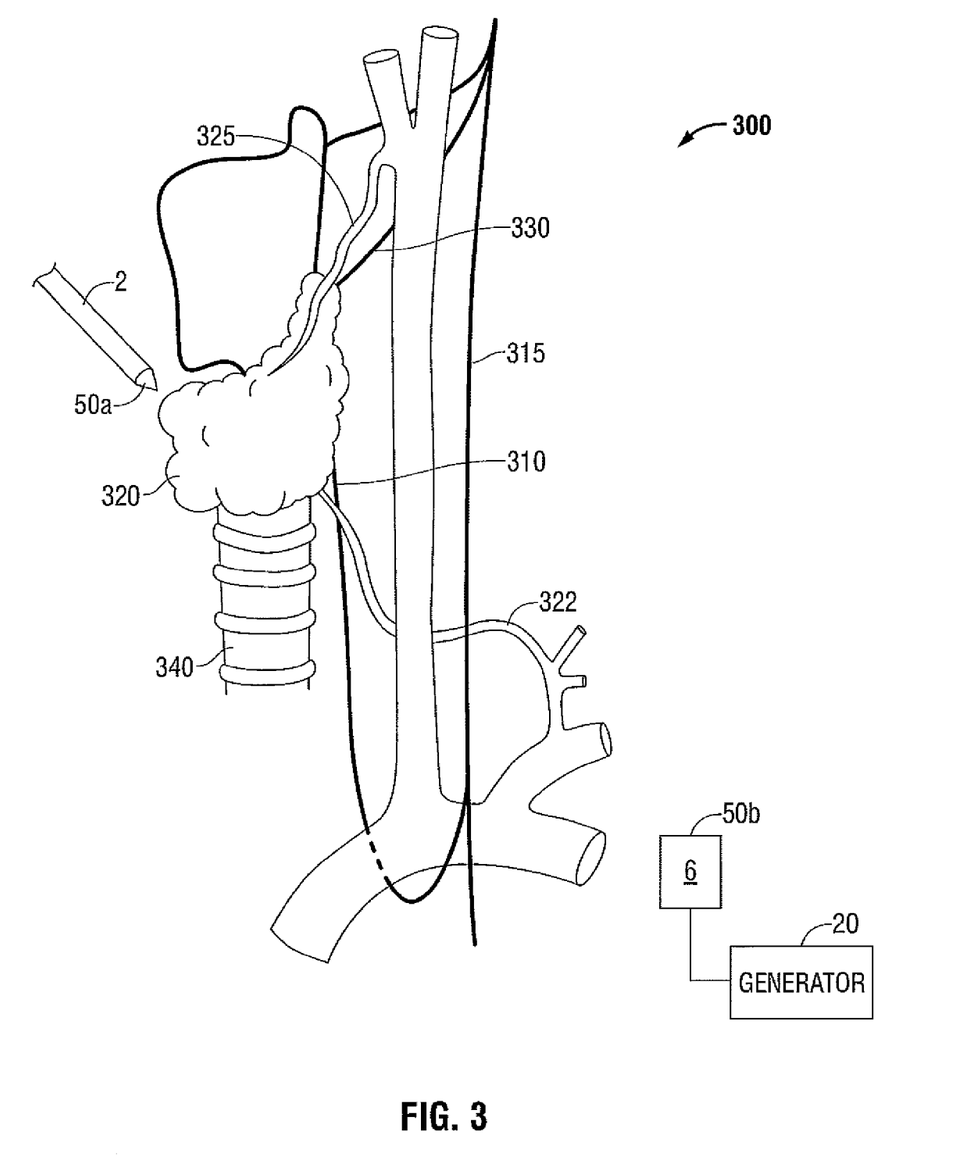
FIG. 3 is a perspective view of a monopolar device and return pad disposed relative to a thyroid region of a patient in accordance with an embodiment of the present disclosure.
Figure 5:
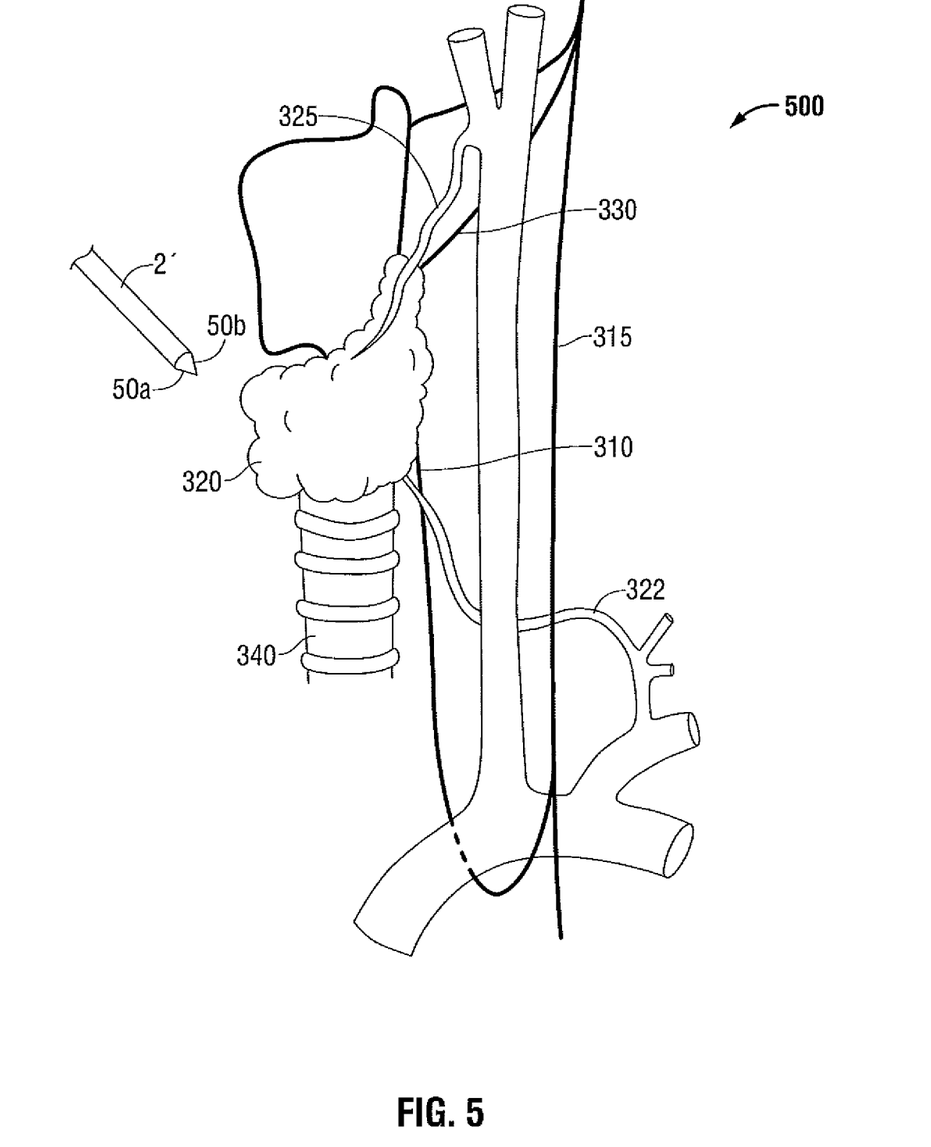
FIG. 5 is a perspective view of a monopolar device disposed relative to a thyroid region of a patient in accordance with another embodiment of the present disclosure.

One example procedure where determining location of the surgical device 2, or 10 relative to a nerve structure is important is a thyroidectomy procedure to remove a thyroid gland from a patient. By way of example, FIGS. 3, 4, and 5 show a general rendering of the thyroid region of a patient to illustrate the presenting of electrosurgical instruments relative to such region. Alternatively, the thyroidectomy procedure may be performed with electrosurgical and/or non-electrosurgical instruments. In this procedure, a surgeon removes either part of the thyroid gland or the entire thyroid gland. However, the thyroid gland is located near the recurrent laryngeal nerve (RLN) 310, and the RLN controls motor function and sensation of the larynx (voice box) (not shown). If the surgical instrument is too close to the RLN 310, then vocal cord paralysis can occur or if both vocal cords are paralyzed, then the opening of the throat may be obstructed causing breathing problems.

Turning now to FIGS. 3-5, various embodiments of electrosurgical instruments that are utilized in conjunction with one or more sensor assemblies 50a, 50b are shown and include, without limitation, monopolar instrument 2 and bipolar forceps 10. Other tools not specifically shown such as a grasper, dissectors/probes, and/or a catheter may also include a sensor assembly 50a, 50b and be used alone or in combination with an electrosurgical instrument in determining the location of a nerve 310, 315, or 330 relative to the tool. Referring initially to FIG. 3, which shows a diagram 300 with a monopolar instrument 2 that includes an active electrode 50a. A receiving electrode 50b is part of the return electrode 6 placed on the outside of patient P's skin. Monopolar instrument 2 is shown near the thyroid gland 320 and as the thyroid gland 320 is removed, the monopolar instrument 2 moves closer to the recurrent laryngeal nerve (RLN) 310. Therefore, as the thyroid gland 320 is removed, the generator 20 periodically sends an electrical signal through sensor 50a and receives the electrical signal through 50b that determines the proximity of the monopolar instrument to the RLN 310, external laryngeal nerve 330, or vargus nerve 315. If the generator 20 determines the instrument 2 is too close to a nerve 310, 315, or 330, then the user is notified through a visual, audible, and/or haptic feedback. The intensity of the notification may increase as the distance decreases to the nerve structure 310, 315, or 330. Alternatively, the generator 20 may cease sending an RF energy signal or other energy signal if the instrument 2 is too close to the nerve structure 310, 315, or 330.

Additionally, the signal sent from the generator 20 through sensor 50a can be used to identify the thyroid gland 320 from the trachea 340, superior thyroid artery 325, the inferior thyroid artery 322, or any nerve structure 310, 315, or 330.

Alternatively, FIG. 5 shows a perspective view of a thyroid gland region 500 with a monopolar instrument 2' that includes an active 50a and a return electrode 50b within the monopolar instrument 2'. The monopolar instrument 2' may be used to determine proximity to any nerve structure 310, 315, or 330 and/or identify the nerve structure 310, 315, or 330 and/or other anatomical structure.

Referring now to FIG. 4, which shows a perspective view of a thyroid gland region 400 and a bipolar instrument 10, electrodes 112, 122 of bipolar forceps 10 are embodied as the active and receiving electrodes 50a, 50b of sensor assembly 50, respectively. Forceps 10 is shown near the thyroid gland 320. As the forceps 10 moves around the thyroid region to excise the thyroid gland 320, a small pulse is sent from the generator 20 to determine the proximity to nerve structures 310, 315, or 330. The small test pulse is sent prior to removing the thyroid gland 320 and while the thyroid gland 320 is being removed. The small test pulse is sent through active electrode 50a and received by return electrode 50b. The generator 20 determines the proximity and notifies the user and/or turns off the energy signal sent to forceps 10. Additionally, after the thyroid gland is removed a test pulse is sent from sensor 50a to RLN 310 to determine if the nerve is functioning properly. Based on the response received by the generator 20 through sensor 50b, the generator determines if the RLN is functioning properly.

Figure 6:
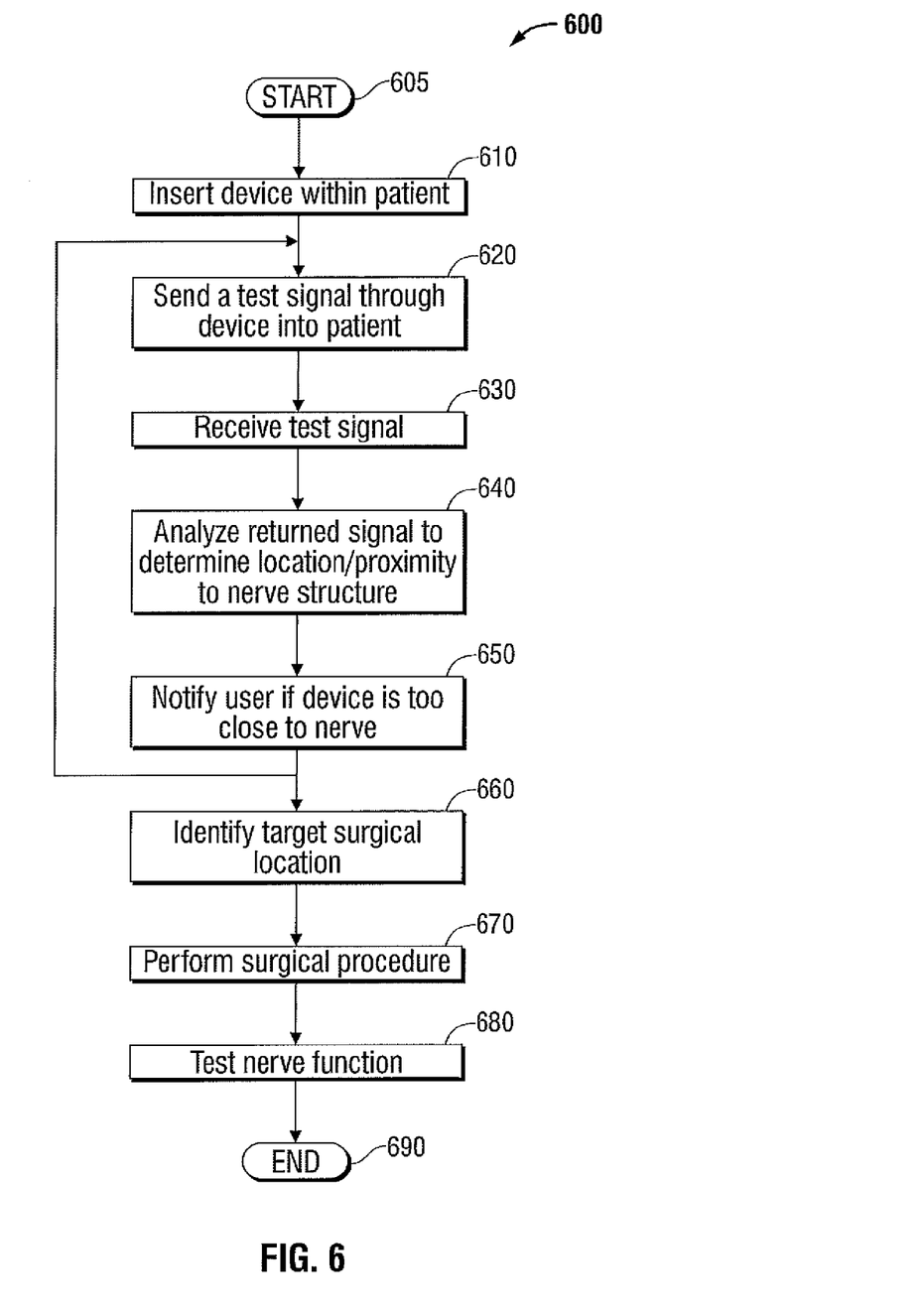
FIG. 6 is a flow chart for locating and identifying a nerve in accordance with an embodiment of the present disclosure.

FIG. 6 shows a flow chart for locating and identifying a nerve structure 310, 315, or 330 during a surgical procedure. The process 600 starts at step 605 and at step 610, the user inserts a surgical device 2, or 10 into the patient P. Next at step 620, a test signal is sent through the surgical device 2, or 10 into the patient P from the generator 20. The generator 20 then receives the test signal from the return electrode 50b at step 630. The generator 20 or an external microcontroller (not shown) analyzes the returned signal to determine the location and/or proximity of the surgical device 2, or 10 to a nerve structure 310, 315, or 330 at step 640. The user is then notified if the surgical device 2, or 10 is too close to the nerve structure 310, 315, or 330 at step 650. Alternatively, the generator 20 may also stop sending the RF energy signal or other energy signal to the surgical device 2, or 10 if the surgical device 2, or 10 is too close to the nerve structure 310, 315, or 330. In one embodiment, steps 620 to 650 are periodically performed as the surgical procedure is performed. Alternatively, steps 620 to 650 may be performed continuously while the surgical procedure is performed by applying a low frequency and a high frequency at the same time. In an another embodiment, a user may select to perform steps 620 to 650 by pressing a button (not shown) on surgical device 2, or 10 and/or the generator 20. At step 660, the target surgical location is identified, such as identifying the thyroid gland 320. Then the surgical procedure is performed at step 670, e.g., removal of the thyroid gland 320. Prior to process 600 ending at step 690, the nerve structure 310, 315, or 330 is tested by the generator 20 at step 680 by sending a test pulse through active electrode 50a and receiving a response through return electrode 50b. Based on the response received, the generator 20 determines if the nerve structure 310, 315, or 330 is functioning properly.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for determining proximity of a surgical device relative to a particular nerve structure, comprising:
   a surgical device having a sensor assembly operably coupled to a processing unit and configured to transmit at least one electrical signal generated by the processing unit through the particular nerve structure to elicit a measurable response therefrom, the surgical device including a pair of opposing jaw members movable relative to each other,
   the processing unit configured to calculate a signature property value of the particular nerve structure based on the measurable response and determine an identity of the particular nerve structure and proximity of the surgical device relative to the particular nerve structure based on a comparison between the signature property value and at least one other signature property value.

2. The system according to claim 1, wherein the measurable response is one of impedance, voltage, electrical conductivity, thermal conductivity, hydraulic conductivity, permittivity, and capacitance of nerve structure.

3. The system according to claim 1, wherein the sensor assembly includes at least one transmitting electrode disposed on the surgical device and at least one receiving electrode disposed on a return electrode, wherein the surgical device is positionable relative to a target anatomical structure.

4. The system according to claim 1, wherein the sensor assembly includes at least one transmitting electrode disposed on the surgical device and the surgical device is a bipolar forceps including:
   a handle configured to actuate the pair of opposing jaw members disposed on a distal end of a shaft extending from the handle, the at least one transmitting electrode disposed on one of the jaw members and the receiving electrode disposed on the opposing jaw member, wherein the transmitting and receiving electrode are also configured to seal tissue grasped between the jaw members.

5. The system according to claim 1, wherein the processing unit is further configured to transmit at least one electrical signal to identify a target anatomical structure.

6. The system according to claim 1, wherein the processing unit is operably coupled to an audio/visual indicator configured to indicate the proximity of the surgical device relative to nerve structure.

7. The system according to claim 1, wherein the processing unit is operably coupled with an electrosurgical generator adapted to supply electrosurgical energy to the surgical device.

8. The system according to claim 7, wherein the processing unit is located within the electrosurgical generator.

\* \* \* \* \*